(12) United States Patent
Rao et al.

(10) Patent No.: US 10,731,138 B2
(45) Date of Patent: Aug. 4, 2020

(54) FORMATE DEHYDROGENASE MUTANT WITH IMPROVED ENZYME ACTIVITY AND STABILITY AND CONSTRUCTION METHOD THEREOF

(71) Applicant: Jiangnan University, Wuxi (CN)

(72) Inventors: Zhiming Rao, Wuxi (CN); Junxian Zheng, Wuxi (CN); Taowei Tao, Wuxi (CN); Junping Zhou, Wuxi (CN); Xian Zhang, Wuxi (CN); Meijuan Xu, Wuxi (CN)

(73) Assignee: Jiangnan University, Wuxi (CN)

( * ) Notice: Subject to any disclaimer, the term of this patent is extended or adjusted under 35 U.S.C. 154(b) by 60 days.

(21) Appl. No.: 16/063,658

(22) PCT Filed: Nov. 14, 2016

(86) PCT No.: PCT/CN2016/105699
§ 371 (c)(1),
(2) Date: Jun. 18, 2018

(87) PCT Pub. No.: WO2018/086118
PCT Pub. Date: May 17, 2018

(65) Prior Publication Data
US 2019/0161741 A1    May 30, 2019

(30) Foreign Application Priority Data
Nov. 8, 2016 (CN) .......................... 2016 1 0978442

(51) Int. Cl.
*C12N 9/02* (2006.01)

(52) U.S. Cl.
CPC .... *C12N 9/0008* (2013.01); *C12Y 102/01002* (2013.01)

(58) Field of Classification Search
None
See application file for complete search history.

(56) References Cited

PUBLICATIONS

Accession AZF02815. Mar. 31, 2011. (Year: 2011).*
Accession A0A0A1EQY0. Feb. 4, 2015 (Year: 2015).*

* cited by examiner

*Primary Examiner* — Christian L Fronda
(74) *Attorney, Agent, or Firm* — IPro, PLLC

(57) ABSTRACT

The present invention discloses a formate dehydrogenase mutant with improved enzyme activity and stability and a construction method thereof, which belongs to the technical field of genetic engineering. The mutant of the present invention is obtained by mutating alanine at a $10^{th}$ site to cysteine based on the amino acid shown in SEQ ID NO. 2. The specific enzyme activity of the mutant enzyme obtained by the present invention is improved by 1.3 times compared with that before the mutation, a half-life period ($t_{1/2}$) at 60° C. is increased by 6.8 times compared with that in the mutation period, the copper ion tolerance is increased by 30 times compared with that before the mutation, and when pH is 4, the stability is improved by 2.0 times, and the catalytic efficiency is increased by 1.4 times. The present invention shows that an amino acid residue at a $10^{th}$ site is mutated to the cysteine which forms a correct disulfide bond with a cysteine residue at a $30^{th}$ site of the natural formate dehydrogenase, so that the stability and the catalytic efficiency of the enzyme are improved, and the industrial application potential of the enzyme is improved.

6 Claims, No Drawings

Specification includes a Sequence Listing.

FORMATE DEHYDROGENASE MUTANT WITH IMPROVED ENZYME ACTIVITY AND STABILITY AND CONSTRUCTION METHOD THEREOF

TECHNICAL FIELD

The disclosure herein relates to the field of genetic engineering, and more particularly relates to a formate dehydrogenase mutant with improved enzyme activity and stability and a construction method thereof.

BACKGROUND

Formate dehydrogenase (FDH, EC 1.2.1.2) catalyzes formic acid to generate carbon dioxide and generates NADH along with the reduction of NAD+. Due to various advantages that the reaction is an irreversible reaction, a substrate is cheap formic acid and a product is CO2 and the like, the formate dehydrogenase is used as a coenzyme cycling system to be usually combined with other oxidordeuctase to be used for the bioconversion production of important optical active compounds such as hydroxy acid, chiral alcohol, amino acid and the like. Wild-type FDH (CboFDH) sourced from *Candida boidinii* is used for regenerating NADH in the production of L-tertiary leucine, which is an example of a maximum application scale of the formate dehydrogenase in the industrialized production at present. Along with the precise parsing of a CboFDH three-dimensional structure, it is possible to reasonably design the CboFDH three-dimensional structure and precisely modify molecules.

The wild-type CboFDH has the disadvantages of low specific enzyme activity and poor operation stability, so that it is of great significance for the chiral compound biosynthesis industry to modify the CboFDH in a site-specific mutagenesis manner, improve the specific enzyme activity and stability and increase the efficiency for regenerating the coenzyme NADH by the CboFDH.

SUMMARY

In order to solve the above-mentioned problems, the present invention provides a formate dehydrogenase mutant with improved enzyme activity and stability and a preparation method thereof.

A first object of the present invention is to provide a formate dehydrogenase mutant with improved enzyme activity and stability, where an amino acid sequence of the formate dehydrogenase mutant is a sequence shown in SEQ ID NO. 1.

The amino acid sequence of the mutant is obtained by mutating the amino acid at a 10th site to cysteine from alanine based on the amino acid with the amino acid sequence shown in SEQ ID NO. 2.

A second object of the present invention is to provide a nucleotide sequence encoding the mutant.

In an embodiment of the present invention, the nucleotide sequence encoding the mutant is a sequence shown in SEQ ID NO. 3.

In an embodiment of the present invention, the nucleotide sequence is obtained by mutating a codon encoding the alanine at the 10th site into a codon encoding the cysteine on the basis of the nucleotide sequence shown in SEQ ID NO. 4.

A third object of the present invention is to provide a recombinant expression vector comprising the nucleotide sequence encoding the mutant.

A fourth object of the present invention is to provide genetically engineered bacteria expressing the formate dehydrogenase mutant.

In an embodiment of the present invention, the genetically engineered bacteria are obtained by connecting the nucleotide sequence shown in SEQ ID NO. 3 to the expression vector to obtain recombinant plasmids, and then convert the recombinant plasmids to host bacteria.

In an embodiment of the present invention, the genetically engineered bacteria are recombinant *Escherichia coli* genetically engineered bacteria.

In an embodiment of the present invention, the expression vector is pET28a.

In an embodiment of the present invention, the host bacteria are *E. coli* BL21.

In an embodiment of the present invention, a preparation method of the genetically engineered bacteria is to mutate a codon encoding alanine at the 10th site into a codon encoding cysteine on the basis of the nucleotide sequence shown in SEQ ID NO. 4 to obtain a recombinant gene, connect the recombinant gene to the expression vector to obtain recombinant plasmids, and convert the recombinant plasmids into *Escherichia coli* BL21 host bacteria, thus obtaining the recombinant genetically engineered bacteria.

In an embodiment of the present invention, the preparation method is specifically as follows:

The nucleotide sequence shown in SEQ ID NO. 4 is adopted as a template, and FIprimer (the sequence is shown in SEQ ID NO. 5) and RIprimer (the sequence is shown in SEQ ID NO. 6) are adopted as primers to perform PCR, thus obtaining the recombinant gene A10C shown in SEQ ID NO. 3.

The recombinant gene sequence obtained in the previous step is connected into the pET28a expression vector to obtain recombinant plasmids pET28a-A10C, and the recombinant plasmids were converted into the *E. coli* BL21 to obtain a recombinant engineering strain named as pET28a-A10C/*E. coli* BL21.

A fifth object of the present invention is to provide a mutant, a nucleotide sequence encoding the mutant, a vector comprising the nucleotide sequence encoding the mutant, and an application of genetically engineered bacteria expressing the mutant.

In an embodiment of the present invention, the application comprises a step of constructing a coenzyme NADH cycling system by combining corresponding dehydrogenase.

In an embodiment of the present invention, the application can be used for regenerating NADH in the bioconversion production of important optical active compounds such as hydroxy acid, chiral alcohol, amino acid and the like.

On the basis of the natural formate dehydrogenase, the molecular structure of the formate dehydrogenase is modified through a site-specific mutagenesis biological technology, the specific enzyme activity of the pure enzyme of the mutant enzyme is improved by 1.3 times compared with that before the mutation, a half-life period (t½) at 60° C. is increased by 6.8 times compared with that in the mutation period, and the copper ion tolerance is improved by 30 times compared with that before the mutation; and meanwhile, the acid resistance of the mutant is also improved, and when the pH is 4, the stability is improved by 2.0 times. Furthermore, the affinity Km of the mutant enzyme A10C to the substrate NAD+ is decreased by 1.4 times compared with that before the mutation, while the affinity Km of the mutant enzyme A10C to the formic acid is not significantly decreased compared with that before the mutation, and the catalytic efficiency (kcat/Km)NAD+ is increased by 1.4 times. The present invention shows that the cysteine obtained by mutating the amino acid residue at 10th site can form a correct disulfide bond with the original cysteine residue at 30th site of the natural formate dehydrogenase, so that the oxidation of the free cysteine is prevented from improving the resistance of the mutant enzyme to copperions (the copper ions are well-known transitional metal ions for promoting the sulfydryl oxidation), and the stability, the specific enzyme activity and the catalytic efficiency are improved. The mutant enzyme obtained by the present invention can be combined with corresponding dehydrogenase to construct the NADH coenzyme cycling system applied to the bioconversion production of optical active compounds and exquisite chemicals.

DETAILED DESCRIPTION

TV fermentation medium: 8 g·L$^{-1}$ of yeast powder, 12 g·L$^{-1}$ of peptone, 4.02 g·L$^{-1}$ of $K_3PO_4$, 3 g·L$^{-1}$ of NaCl, 2 g·L$^{-1}$ of citric acid, 0.3 g·L$^{-1}$ of ammonium ferric citrate, 10 g·L$^{-1}$ of glycerinum, 2.5 g·L$^{-1}$ of $(NH_4)_2SO_4$, and $MgSO_4·7H_2O_2$. The pH was adjusted to 7.2.

Definition of enzyme activity: an enzyme amount required by reducing 1 μmol of NAD$^+$ to NADH in every one minute was defined as one enzyme activity unit U. The specific enzyme activity was defined as the enzyme activity U·mg$^{-1}$ of per unit protein.

Method for determining enzyme activity of formate dehydrogenase: a reaction system was 10 mmol·L$^{-1}$ of potassium phosphate buffer solution with the pH being 7.5 which contains 1.67 mmol·L$^{-1}$ of NAD and 167 mmol·L$^{-1}$ of sodium formate. An appropriate amount of enzyme liquid was added to initiate the reaction, the reaction was performed for 1.5 minutes at 30° C., an absorbance value at 340 nm was measured every 30 s, and the data was recorded. The concentration of NADH was calculated according to the increment of the absorbance value at 340 nm of the reaction solution, the enzyme activity was calculated, and a reaction formula was as follows: $NaCOOH+NAD^+=CO_2+NADH+Na^+$.

Example 1: Construction of a Recombinant Vector Comprising the Formate Dehydrogenase Mutant (1) Acquisition of mutant A10C: the nucleotide sequence shown in SEQ ID NO. 4 was adopted as a template, and F primer (the sequence was shown in SEQ ID NO. 5) and R primer (the sequence was shown in SEQ ID NO. 6) were adopted as primers to perform PCR, thus obtaining the recombinant gene shown in SEQ ID NO. 3.

(2) The recombinant gene and pET28a were bi-digested by utilizing EcoRI and XhoI and were ligated overnight at 16° C. by utilizing T4 DNA ligase after being purified. A ligation product was converted into E. coli BL21 competent cells in a chemical method. A conversion solution was smeared on an LB flat panel containing kanamycin (50 mg·L$^{-1}$), plasmids were extracted, and the constructed recombinant plasmids were verified by virtue of double-restriction enzyme digestion and were named as pET28a-A10C. Sequencing work was carried out by Shanghai Sangon Biotech.

Example 2: Construction of Recombinant Escherichia Coli Engineered Bacteria Producing the Formate Dehydrogenase Mutant A strain comprising correct recombinant plasmids pET28a-A10C obtained in the embodiment 1 was the recombinant gene engineered bacteria pET28a-A10C/E. coli BL21 of the present invention.

Example 3: Express Formate Dehydrogenase with Recombinant Bacteria pET28a-A10c/E. coli Bl21 and Enzyme Activity Determination The recombinant bacteria pET28a-A10C/E. coli BL21 constructed in the embodiment 2 and a reference strain pET28a-FDH/E. coli BL21 expressing non-mutated wild enzyme CboFDH (amino acid sequence was shown in SEQ ID NO.2) were separately inoculated into 10 mL of LB culture medium containing kanamycin, were oscillated at 37° C. and cultured overnight to be transferred into a TY fermentation medium at a subsequent day in an amount of 4% of the inoculation amount, and were induced for 16 hours at 24° C. with the addition of 0.5 mM of IPTG after being cultured at 37° C. for 4 h. Cells were collected by centrifuge and disrupted, and the cell supernatant (crude enzyme liquid) was used for determining the enzyme activity.

The obtained crude enzyme liquid was purified to obtain the formate dehydrogenase mutant A10C, kinetic parameters of the purified recombinant formate dehydrogenase mutant A10C were analyzed, as shown in table 1, the affinity $K_m$ of the mutant enzyme A10C to the substrate NAD$^+$ was decreased by 1.4 times compared with that before the mutation, while the affinity $K_m$ of the mutant enzyme A10C to the substrate formic acid was not significantly decreased compared with that before the mutation, the catalytic efficiency $(k_{cat}/K_m)^{NAD+}$ was increased by 1.4 times, and the specific enzyme activity was improved by 1.3 times co pared with that before the mutation.

TABLE 1

A10C reaction kinetic parameters

| Enzyme | Km NAD (μM) | Km formate (mM) | kcat (s$^{-1}$) | (kcat/Km) NAD (μM$^{-1}$ s$^{-1}$) | Specific enzyme activity (U mg$^{-1}$) |
|---|---|---|---|---|---|
| CboFDH | 53.6 ± 3.4 | 7.3 ± 0.6 | 3.3 ± 0.3 | 0.06 | 5.6 ± 0.4 |
| A10C | 74.2 ± 2.6 | 8.2 ± 0.4 | 6.2 ± 0.5 | 0.08 | 7.4 ± 0.5 |

The copper ion tolerance of the obtained pure enzyme was analyzed, the enzyme activities of the wild-type CboFDH and the mutant enzyme A10C under the condition of different concentrations of copperions were detected, where the required concentration of the copper ions was 15 mM when the residual enzyme activity of the mutant enzyme was 50%, and the required concentration of the copper ions was smaller than 0.5 mM when the residual enzyme activity of the wild-type enzyme CboFDH was 50%. This showed that the tolerance of the mutant enzyme A10C to the copper ions was increased by more than 30 times.

Thermal stability analysis was carried out on the obtained pure enzyme, and the pure enzyme was hatched for different times at the temperature of 60° C., the half-life period of the mutant enzyme was 21.6 min and was increased by 6.8 times compared with the wild-type CboFDH (3.2 min).

PH stability analysis was carried out on the obtained pure enzyme, and the obtained pure enzyme was hatched for 1 h under the condition of different pH, it was discovered that the residual enzyme activity of the mutant enzyme A10C under the acid addition was higher than the wild-type enzyme CboFDH, where when the pH was 4, the residual enzyme activity of the mutant enzyme A10C was 89.2%, while the residual enzyme activity of the wild-type enzyme CboFDH was only 45.3%.

What is claimed is:

1. A formate dehydrogenase mutant comprising amino acid sequence SEQ ID NO. 1.

2. The formate dehydrogenase mutant of claim 1, wherein the mutant possesses a specific enzyme activity in pure form that is improved by 1.3 times as compared with wild type formate dehydrogenase measured under identical conditions.

3. The formate dehydrogenase mutant of claim 1, wherein the mutant possesses a half-life period at 60° C. that is increased by 6.8 times as compared with wild type formate dehydrogenase measured under identical conditions.

4. The formate dehydrogenase mutant of claim 1, wherein protein stability of the mutant is improved by two fold at pH 4 as compared with wild type formate dehydrogenase measured under identical conditions.

5. The formate dehydrogenase of claim 1, wherein the mutant possesses a Km for NAD+ that is decreased by 1.4 fold as compared with wild type formate dehydrogenase measured under identical conditions.

6. The formate dehydrogenase of claim 1, wherein the mutant possesses a catalytic efficiency (kcat/Km) for NAD+ that is increased by 1.4 fold as compared with wild type formate dehydrogenase measured under identical conditions.

* * * * *

SEQUENCE LISTING

<160> NUMBER OF SEQ ID NOS: 6

<210> SEQ ID NO 1
<211> LENGTH: 364
<212> TYPE: PRT
<213> ORGANISM: Artificial Sequence
<220> FEATURE:
<223> OTHER INFORMATION: Protein translated from Synthetic DNA

<400> SEQUENCE: 1

```
Met Lys Ile Val Leu Val Leu Tyr Asp Cys Gly Lys His Ala Ala Asp
1               5                   10                  15

Glu Glu Lys Leu Tyr Gly Cys Thr Glu Asn Lys Leu Gly Ile Ala Asn
            20                  25                  30

Trp Leu Lys Asp Gln Gly His Glu Leu Ile Thr Thr Ser Asp Lys Glu
        35                  40                  45

Gly Gly Asn Ser Val Leu Asp Gln His Ile Pro Asp Ala Asp Ile Ile
    50                  55                  60

Ile Thr Thr Pro Phe His Pro Ala Tyr Ile Thr Lys Glu Arg Ile Asp
65                  70                  75                  80

Lys Ala Lys Lys Leu Lys Leu Val Val Ala Gly Val Gly Ser Asp
                85                  90                  95

His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
        115                 120                 125

Met Thr Met Leu Val Leu Val Arg Asn Phe Val Pro Ala His Glu Gln
    130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Val Pro Phe Asn Pro Lys Glu Leu Leu
            180                 185                 190

Tyr Tyr Asp Tyr Gln Ala Leu Pro Lys Asp Ala Glu Glu Lys Val Gly
        195                 200                 205

Ala Arg Arg Val Glu Asn Ile Glu Glu Leu Val Ala Gln Ala Asp Ile
    210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Cys Val Ala Glu Asp Val Ala Ala Leu Glu
            260                 265                 270

Ser Gly Gln Leu Arg Gly Tyr Gly Gly Asp Val Trp Phe Pro Gln Pro
        275                 280                 285

Ala Pro Lys Asp His Pro Trp Arg Asp Met Arg Asn Lys Tyr Gly Ala
    290                 295                 300

Gly Asn Ala Met Thr Pro His Tyr Ser Gly Thr Thr Leu Asp Ala Gln
305                 310                 315                 320

Thr Arg Tyr Ala Gln Gly Thr Lys Asn Ile Leu Glu Ser Phe Phe Thr
                325                 330                 335
```

-continued

Gly Lys Phe Asp Tyr Arg Pro Gln Asp Ile Ile Leu Leu Asn Gly Glu
              340                 345                 350

Tyr Val Thr Lys Ala Tyr Gly Lys His Asp Lys Lys
              355                 360

<210> SEQ ID NO 2
<211> LENGTH: 364
<212> TYPE: PRT
<213> ORGANISM: Artificial Sequence
<220> FEATURE:
<223> OTHER INFORMATION: Protein translated from Synthetic DNA

<400> SEQUENCE: 2

Met Lys Ile Val Leu Val Leu Tyr Asp Ala Gly Lys His Ala Ala Asp
1               5                   10                  15

Glu Glu Lys Leu Tyr Gly Cys Thr Glu Asn Lys Leu Gly Ile Ala Asn
            20                  25                  30

Trp Leu Lys Asp Gln Gly His Glu Leu Ile Thr Thr Ser Asp Lys Glu
        35                  40                  45

Gly Gly Asn Ser Val Leu Asp Gln His Ile Pro Asp Ala Asp Ile Ile
    50                  55                  60

Ile Thr Thr Pro Phe His Pro Ala Tyr Ile Thr Lys Glu Arg Ile Asp
65                  70                  75                  80

Lys Ala Lys Lys Leu Lys Leu Val Val Ala Gly Val Gly Ser Asp
                85                  90                  95

His Ile Asp Leu Asp Tyr Ile Asn Gln Thr Gly Lys Lys Ile Ser Val
            100                 105                 110

Leu Glu Val Thr Gly Ser Asn Val Val Ser Val Ala Glu His Val Val
        115                 120                 125

Met Thr Met Leu Val Leu Val Arg Asn Phe Val Pro Ala His Glu Gln
    130                 135                 140

Ile Ile Asn His Asp Trp Glu Val Ala Ala Ile Ala Lys Asp Ala Tyr
145                 150                 155                 160

Asp Ile Glu Gly Lys Thr Ile Ala Thr Ile Gly Ala Gly Arg Ile Gly
                165                 170                 175

Tyr Arg Val Leu Glu Arg Leu Val Pro Phe Asn Pro Lys Glu Leu Leu
            180                 185                 190

Tyr Tyr Asp Tyr Gln Ala Leu Pro Lys Asp Ala Glu Glu Lys Val Gly
        195                 200                 205

Ala Arg Arg Val Glu Asn Ile Glu Glu Leu Val Ala Gln Ala Asp Ile
    210                 215                 220

Val Thr Val Asn Ala Pro Leu His Ala Gly Thr Lys Gly Leu Ile Asn
225                 230                 235                 240

Lys Glu Leu Leu Ser Lys Phe Lys Lys Gly Ala Trp Leu Val Asn Thr
                245                 250                 255

Ala Arg Gly Ala Ile Cys Val Ala Glu Asp Val Ala Ala Ala Leu Glu
            260                 265                 270

Ser Gly Gln Leu Arg Gly Tyr Gly Gly Asp Val Trp Phe Pro Gln Pro
        275                 280                 285

Ala Pro Lys Asp His Pro Trp Arg Asp Met Arg Asn Lys Tyr Gly Ala
    290                 295                 300

Gly Asn Ala Met Thr Pro His Tyr Ser Gly Thr Thr Leu Asp Ala Gln
305                 310                 315                 320

Thr Arg Tyr Ala Gln Gly Thr Lys Asn Ile Leu Glu Ser Phe Phe Thr
                325                 330                 335

Gly Lys Phe Asp Tyr Arg Pro Gln Asp Ile Ile Leu Leu Asn Gly Glu
                340                 345                 350

Tyr Val Thr Lys Ala Tyr Gly Lys His Asp Lys Lys
                355                 360

<210> SEQ ID NO 3
<211> LENGTH: 1095
<212> TYPE: DNA
<213> ORGANISM: Artificial Sequence
<220> FEATURE:
<223> OTHER INFORMATION: Synthetic DNA

<400> SEQUENCE: 3

| | |
|---|---:|
| atgaagatcg ttttagtctt atacgattgt ggtaagcacg ctgccgatga agaaaaatta | 60 |
| tacggttgta ctgaaaacaa attaggtatt gccaattggt tgaaagatca aggacatgaa | 120 |
| ttaatcacca cgtctgataa agaaggcgga aacagtgtgt ggatcaaca taccagat | 180 |
| gccgatatta tcattacaac tcctttccat cctgcttata tcactaagga aagaatcgac | 240 |
| aaggctaaaa aattgaaatt agttgttgtc gctggtgtcg ttctgatca tattgatttg | 300 |
| gattatatca accaaaccgg taagaaaatc tccgttttgg aagttaccgg ttctaatgtt | 360 |
| gtctctgttg cagaacacgt tgtcatgacc atgcttgtct tggttagaaa ttttgttcca | 420 |
| gctcacgaac aaatcattaa ccacgattgg gaggttgctg ctatcgctaa ggatgcttac | 480 |
| gatatcgaag gtaaaactat cgccaccatt ggtgccggta aattggtta cagagtcttg | 540 |
| gaaagattag tcccattcaa tcctaaagaa ttattatact cgattatca agctttacca | 600 |
| aaagatgctg aagaaaagt tggtgctaga agggttgaaa atattgaaga attggttgcc | 660 |
| caagctgata tagttacagt taatgctcca ttcacacgctg gtacaaaagg tttaattaac | 720 |
| aaggaattat tgtctaaatt caagaaaggt gcttggttag tcaatactgc aagaggtgcc | 780 |
| atttgtgttg ccgaagatgt tgctgcagct ttagaatctg gtcaattaag aggttatggt | 840 |
| ggtgatgttt ggttcccaca accagctcca aaagatcacc catggagaga tatgagaaac | 900 |
| aaatatggtg ctggtaacgc catgactcct cattactctg gtactacttt agatgctcaa | 960 |
| actagatacg ctcaaggtac taaaaatatc ttggagtcat tctttactgg taagtttgat | 1020 |
| tacagaccac aagatatcat cttattaaac ggtgaatacg ttaccaaagc ttacggtaag | 1080 |
| cacgataaga aataa | 1095 |

<210> SEQ ID NO 4
<211> LENGTH: 1095
<212> TYPE: DNA
<213> ORGANISM: Artificial Sequence
<220> FEATURE:
<223> OTHER INFORMATION: Synthetic DNA

<400> SEQUENCE: 4

| | |
|---|---:|
| atgaagatcg tttagtctt atacgatgct ggtaagcacg ctgccgatga agaaaaatta | 60 |
| tacggttgta ctgaaaacaa attaggtatt gccaattggt tgaaagatca aggacatgaa | 120 |
| ttaatcacca cgtctgataa agaaggcgga aacagtgtgt ggatcaaca taccagat | 180 |
| gccgatatta tcattacaac tcctttccat cctgcttata tcactaagga aagaatcgac | 240 |
| aaggctaaaa aattgaaatt agttgttgtc gctggtgtcg ttctgatca tattgatttg | 300 |
| gattatatca accaaaccgg taagaaaatc tccgttttgg aagttaccgg ttctaatgtt | 360 |
| gtctctgttg cagaacacgt tgtcatgacc atgcttgtct tggttagaaa ttttgttcca | 420 |

```
gctcacgaac aaatcattaa ccacgattgg gaggttgctg ctatcgctaa ggatgcttac    480
gatatcgaag gtaaaactat cgccaccatt ggtgccggta gaattggtta cagagtcttg    540
gaaagattag tcccattcaa tcctaaagaa ttattatact acgattatca agctttacca    600
aaagatgctg aagaaaaagt tggtgctaga agggttgaaa atattgaaga attggttgcc    660
caagctgata tagttacagt taatgctcca ttacacgctg gtacaaaagg tttaattaac    720
aaggaattat tgtctaaatt caagaaaggt gcttggttag tcaatactgc aagaggtgcc    780
atttgtgttg ccgaagatgt tgctgcagct ttagaatctg gtcaattaag aggttatggt    840
ggtgatgttt ggttcccaca accagctcca aaagatcacc catggagaga tatgagaaac    900
aaatatggtg ctggtaacgc catgactcct cattactctg gtactacttt agatgctcaa    960
actagatacg ctcaaggtac taaaaatatc ttggagtcat tctttactgg taagtttgat   1020
tacagaccac aagatatcat cttattaaac ggtgaatacg ttaccaaagc ttacggtaag   1080
cacgataaga aataa                                                    1095

<210> SEQ ID NO 5
<211> LENGTH: 46
<212> TYPE: DNA
<213> ORGANISM: Artificial Sequence
<220> FEATURE:
<223> OTHER INFORMATION: Synthetic DNA

<400> SEQUENCE: 5
ggaattcatg aagatcgttt tagtcttata cgattgtggt aaacac                    46

<210> SEQ ID NO 6
<211> LENGTH: 33
<212> TYPE: DNA
<213> ORGANISM: Artificial Sequence
<220> FEATURE:
<223> OTHER INFORMATION: Synthetic DNA

<400> SEQUENCE: 6
ccctcgagtt atttcttatc gtgcttacca taa                                  33
```